United States Patent
Millar et al.

[11] Patent Number: 5,902,248
[45] Date of Patent: May 11, 1999

[54] REDUCED SIZE CATHETER TIP MEASUREMENT DEVICE

[75] Inventors: Huntly D. Millar; Richard Alan Smith, both of Houston, Tex.

[73] Assignee: Millar Instruments, Inc., Houston, Tex.

[21] Appl. No.: 08/744,478

[22] Filed: Nov. 6, 1996

[51] Int. Cl.$^6$ .................................................. A61B 5/02
[52] U.S. Cl. ......................... 600/485; 600/561; 73/721; 73/727
[58] Field of Search ..................... 600/488, 485, 600/486, 561; 73/720, 721, 726, 727, 777, 715

[56] References Cited

U.S. PATENT DOCUMENTS

| | | | |
|---|---|---|---|
| 3,277,718 | 10/1966 | Ruge | 73/398 |
| 3,315,201 | 4/1967 | Werme | 338/2 |
| 3,417,361 | 12/1968 | Heller et al. | 338/42 |
| 3,480,003 | 11/1969 | Crites | 128/2 |
| 3,550,583 | 12/1970 | Chiku et al. | 128/2.05 |
| 3,553,625 | 1/1971 | Stedman | 338/4 |
| 3,710,781 | 1/1973 | Huthcins, IV et al. | 128/675 |
| 3,946,724 | 3/1976 | La Balme | 128/2.05 E |
| 4,023,562 | 5/1977 | Hynecek et al. | 128/2.05 E |
| 4,274,423 | 6/1981 | Mizuno et al. | 128/675 |
| 4,665,925 | 5/1987 | Millar | 128/663 |
| 4,722,348 | 2/1988 | Ligtenberg et al. | 128/675 |
| 4,771,782 | 9/1988 | Millar | 128/637 |
| 4,878,898 | 11/1989 | Griffin et al. | 604/101 |
| 4,941,473 | 7/1990 | Tenerz et al. | 128/637 |
| 5,207,103 | 5/1993 | Wise et al. | 600/488 |
| 5,352,223 | 10/1994 | McBrayer et al. | 606/51 |
| 5,431,628 | 7/1995 | Millar | 604/100 |
| 5,564,434 | 10/1996 | Halperin et al. | 600/488 |
| 5,688,267 | 11/1997 | Panescu et al. | 606/31 |

OTHER PUBLICATIONS

McDermott, et al. "Monitoring Acute Compartment Pressures with S.T.I.C. Catheter," *Clinical Orthopaedics and Related Research*, 190:192–198, 1984.

Geddes, L.A. "Direct Measurement of Blood Pressure" In: *The Direct and Indirect Measurement of Blood Pressure*, Yr. Book Med. Publ., Inc., 1970, pp. 33–34 only.

Millar Instruments, Inc. Mikro–Tip Catheter Tranndsucers brochure, 1994.

*Primary Examiner*—Michael Peffley
*Assistant Examiner*—Bryan K. Yarnell
*Attorney, Agent, or Firm*—Arnold White & Durkee

[57] ABSTRACT

A device that contemplates a unique and advantageous reduced size catheter tip measurement device. By using a bottom support member and a thin outer insulating layer, rather than a tubular metal casing, to support and isolate the electrical measurement sensor, the present invention drastically reduces feature size possible with current structures for catheter tip measurement devices. More specifically, the device contemplates a reduced size catheter tip pressure transducer device. The device includes a catheter body that has a support member attached to its distal tip. The support member has a support surface for a semiconductor pressures sensor that provides mechanical stability to the pressure sensor. The exposed electrical and metal areas of the device are insulated from surrounding tissues and fluids by an outer insulating layer, which is preferably a polyimide sleeve. Utilizing the device catheter tip pressure transducers may be constructed having approximately half the current volume size of prior devices. This drastic reduction is size allows for placement inside small diameter lumens of catheters, small diameter veins and arteries, or other small biological features that have up to now been too small for high-fidelity measurements by prior catheter tip pressure transducers.

13 Claims, 3 Drawing Sheets

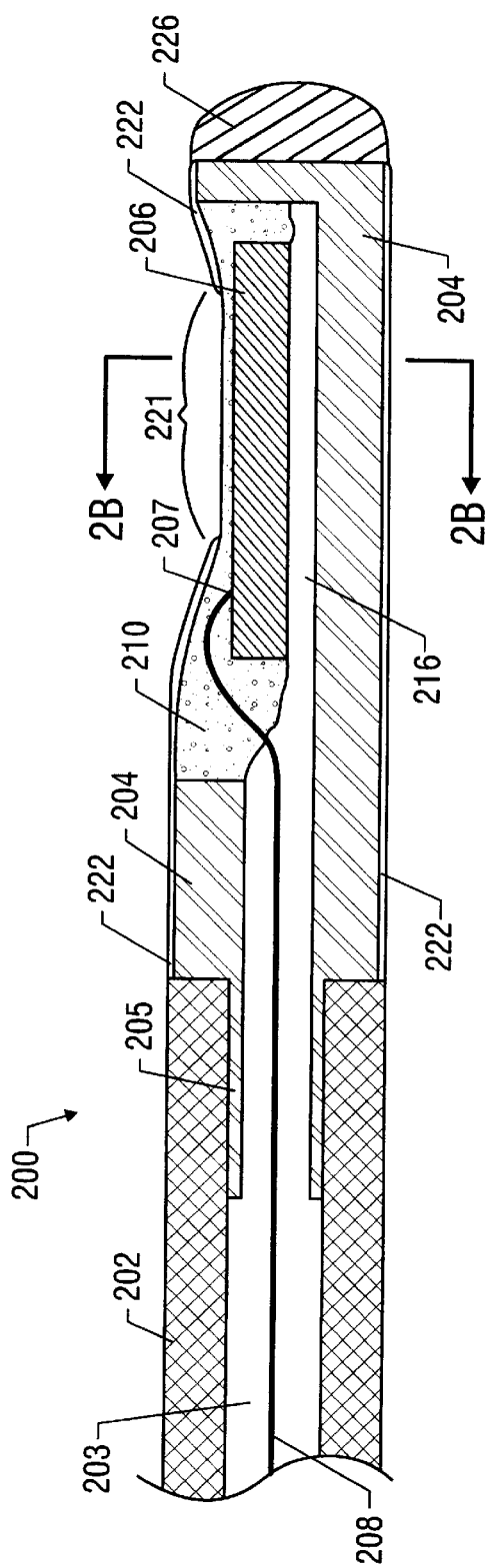
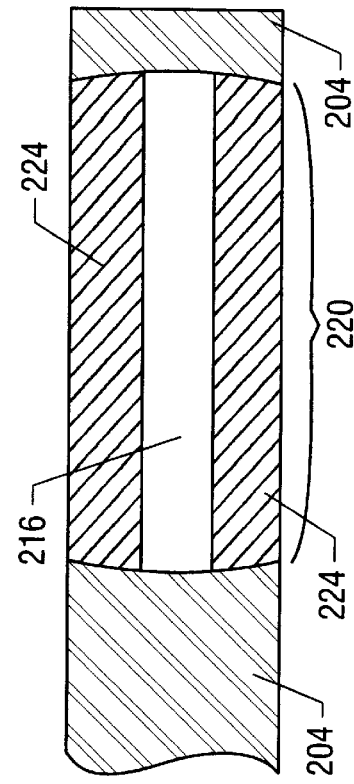
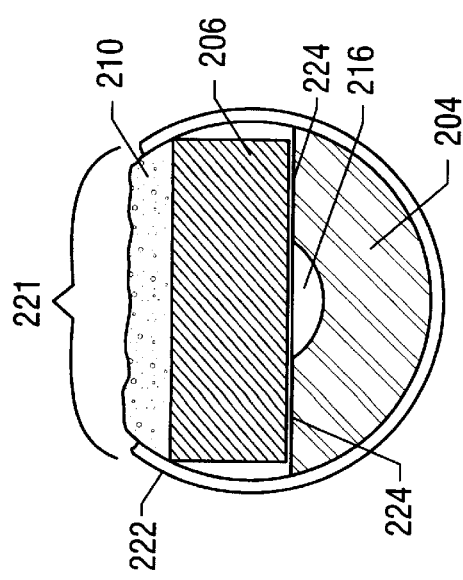
FIG. 2A
FIG. 2C
FIG. 2B

REDUCED SIZE CATHETER TIP MEASUREMENT DEVICE

BACKGROUND OF THE INVENTION

The invention relates to reducing the size of catheter tip measurement devices that are inserted into body organs to make internal measurements. More specifically, the invention relates to the mechanism for supporting and insulating an electrical measurement sensor, particularly a semiconductor strain gauge pressure transducer, that is located at the distal tip of a catheter tip measurement device.

Catheter tip measurement devices are catheters that have measurement sensors located at or near their distal tips. These devices are used in a variety of applications to measure internal properties of internal tissues and fluids such as blood volume, velocity and pressure. Catheter tip measurement devices may be introduced directly into arteries, veins or other body organs either by themselves or through other catheters that have been previously positioned within a patient. Catheter tip measurement devices generally have electrical or fiber optic connectors at the proximal end of the catheter that communicate data from the measurement sensors to external processing devices. Catheter tip pressure transducers are catheter tip measurement devices that have at least one pressure transducer located at or near the distal tip of the catheter.

The size of the catheter tip is important, and for many applications, this size is the primary limiting factor that determines whether a measurement catheter may be used in a particular application. For example, size is important and is a limiting factor in measuring pressure within small vessels, such as coronary arteries. Size is also important where a catheter tip measurement device is being introduced through the lumen of another catheter. One such application is where a small sized catheter tip pressure transducer is introduced through the lumen of an electrode or conductance catheter. A conductance catheter has electrodes disposed at the distal end of the catheter to measure electrical currents. These measurements can be translated into volume and impedance measurements of heart segments on a beat-by-beat basis. A catheter tip pressure transducer introduced through the lumen of a conductance catheter allows for simultaneous measurement of pressure at the tip of the conductance catheter. In this way, the conductance catheter can be used for volume measurements, and the catheter tip pressure transducer can be used for pressure measurements. The resulting pressure/volume loops are of significant diagnostic value in many types of heart disease.

Studies involving small animals are further important applications where a small catheter size is desirable and often required. Although small sized fluid-filled catheters may be used for internal pressure measurements, they are typically reliable only when catheters with relatively large lumens are used and when slow heart beat rates are involved. In small animals, however, the heart beat rates are typically very fast, and the organ size is very small. The internal fluid-filled lumen of the fluid-filled catheter will generally be so small in such applications that the pressure signals received will tend to be extremely damped and unreliable. Although prior catheter tip pressure transducers provide the desired high-fidelity, prior devices have been too large for small animal applications. As more and more research is being done on mice instead of larger animals such as rats, dogs or monkeys, the need for small catheters capable of providing high fidelity internal pressure measurements will continue to increase.

Present small-size catheter devices capable of making internal pressure measurements take the form of fluid-filled devices, electrical strain gauge type transducer devices, and fiber optic devices. Fluid-filled devices may have very small construction, but such devices provide poor measurement fidelity. Similarly, fiber optic devices have a very small sensor size, but such devices have relatively unstable and unacceptable performance. In contrast, strain gauge type transducer devices, which utilize semiconductor pressure transducers, provide high-fidelity measurements but suffer from requiring a significantly larger feature size.

What is needed, therefore, is a catheter tip pressure transducer device that provides high-fidelity measurements with the stability of electrical strain gauge devices and with a very small feature size. What is also, and more generally, needed is the capability of reducing the tip size of catheter tip measurement devices.

SUMMARY OF THE INVENTION

The present invention achieves these goals with a unique and advantageous structure for a catheter tip measurement device that provides high-fidelity measurement capabilities and an extremely small size. In particular, the invention drastically reduces the volume and diameter required for catheter tip measurement devices by using a bottom support member and a thin layer of insulating material for isolating it from surrounding tissue in place of a significantly larger metal casing housing used by prior devices. Although the present invention may be used with different measurement devices, it is believed particularly advantageous for use with pressure transducers, including semiconductor strain gauge type pressure transducers. Utilizing the present invention, catheter tip pressure transducers may be constructed having approximately half the current volume size of prior devices. This drastic reduction in size allows for placement inside small diameter lumens of catheters, small diameter veins and arteries, or other small biological features that have up to now been too small for high-fidelity measurements by prior catheter tip pressure transducers.

The present invention also provides a unique and advantageous housing assembly that greatly reduces the size of catheter tip measurement devices that use other electrical sensing devices. By using a bottom support member and a thin outer insulating layer, rather than a metal casing, to support and isolate the electrical sensors the present invention drastically reduces feature size. Thus, the present invention achieves a significantly smaller housing structure for electrical sensors than was achieved with prior structures and, therefore, provides significant advantages in applications even where an extremely small feature size may not be required.

In one embodiment, the present invention contemplates a catheter tip pressure transducer device having a catheter body and a support member. The catheter body has at least one internal lumen that provides access to an external reference pressure. The support member is attached to the distal tip of the catheter body and has a support surface. A venting channel is disposed within the support surface of the support member and communicates with the internal lumen of the catheter body. A semiconductor pressure sensor, having a diaphragm with a sensing side and a reference side, is supported by said support surface and is positioned relative to the venting channel so that the reference side of said diaphragm is in communication with the venting channel. A flexible insulating material is disposed over the sensing side of the diaphragm of the pressure sensor. An outer insulating layer then covers exposed areas of the pressure sensor except for the sensing side of the diaphragm of the pressure sensor.

In one more specific embodiment, the outer insulating layer surrounds the entire distal tip of said device including said support member and said pressure sensor and may be a polyimide sleeve. Furthermore, the support surface of the support member may be a tubular metal casing including a generally U-shaped portion providing the support surface with the venting channel. More particularly, the width of the support surface of the support member is approximately the width of the semiconductor pressure sensor. The end of the support member may also be sealed by an epoxy bead coupled to a tip of said support member.

In one further embodiment, the catheter tip pressure transducer device also includes at least one electrode disposed adjacent the distal end of the device and a portion of the support member, if metal, may be one electrode. An electrode may also be disposed in the catheter body.

More generally, the present invention is a catheter tip measurement device including a catheter body and a support member attached to the distal tip of the catheter body. The support member has a support surface that supports a measurement sensor.

An outer insulating layer covering exposed electrical areas of said measurement sensor. More particularly, the support surface of the support member is the generally planar top surface of a generally U-shaped member. In another embodiment, the support member may be made from a ceramic material.

BRIEF DESCRIPTION OF THE DRAWINGS

It is to be noted that the appended drawings illustrate only particular embodiments of the invention and are, therefore, not to be considered limiting of its scope, for the invention may admit to other effective embodiments.

FIG. 2A is a center-line side cross-section view of a catheter tip measurement device according to the present invention.

FIG. 2B is an end cross-section view along line A—A of a catheter tip measurement device according to the present invention.

FIG. 2C is a top view of a support for a catheter tip measurement device according to the present invention.

DETAILED DESCRIPTION

The primary limiting factor in reducing the size of catheter tip measurement devices has been the casing used to surround, isolate and insulate the measurement devices at the distal end of the catheter. For example, prior catheter tip measurement devices with semiconductor strain gauge type pressure sensors have been limited to approximately 0.025 inches in the outer diameter (O.D.) of the catheter tip.

Small strain gauge type pressure sensors may be made from semiconductor material, such as silicon. These semiconductor devices are generally shaped like a brick, have a strain gauge diaphragm, and include circuitry for providing electrical signals representative of the pressure sensed by the strain gauge to pads that may be connected to external devices. In operation, one side of the strain gauge diaphragm is equalized to a reference pressure, such as atmospheric pressure (the reference side), and the other side of the strain gauge diaphragm is exposed to the body tissues or fluids (sensing side). Such semiconductor strain gauge pressure sensors provide high-fidelity pressure measurements. The size of these semiconductor devices, however, is limited by mechanical considerations. Presently the smallest commercial device is approximately 0.016 inches wide, 0.036 inches long, and 0.006 inches thick.

In mounting a semiconductor pressure sensor to a catheter, it has been important to isolate the pressure sensor from mechanical movement and mechanical stresses that might sufficiently deform the sensor to give false pressure readings. The primary prior technique for mounting a semiconductor pressure sensor to the end of a catheter tip measurement device has been to use a tubular metal casing, such as a portion of a stainless steel hypodermic needle. With this sturdy metal casing surrounding the sensor, the sensor was isolated from catheter movement and was sensitive only to external sensing pressure. The proximal end of the metal casing was connected to the catheter body and was open to allow electrical connections from the catheter to reach the semiconductor pressure sensor. The proximal end was also open to allow venting of the back of the reference side of the strain gauge diaphragm to an external pressure through a lumen in the catheter body. With such prior devices, a window was generally cut into the side of the tubular metal casing. The sensing side of the strain gauge diaphragm of the sensor was left exposed through the window to applied external pressures from body fluids and tissues.

Figure 1A:
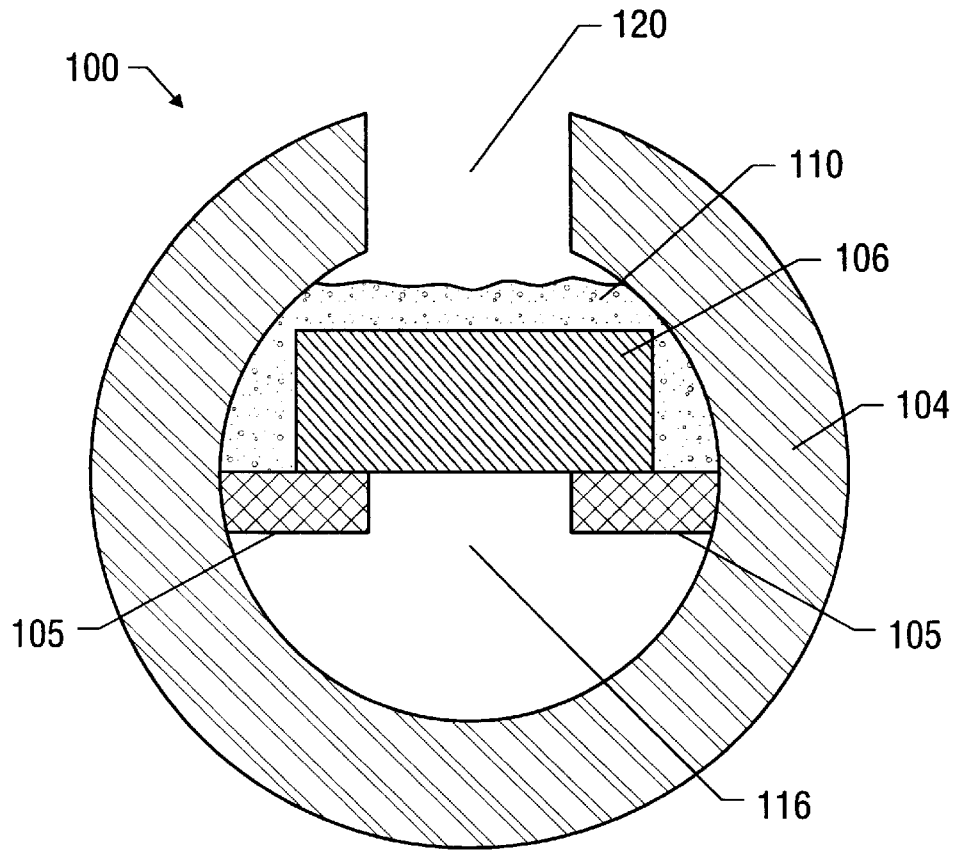
FIG. 1A (prior art) is an end cross-section view of a prior art catheter tip measurement device.
Figure 1B:
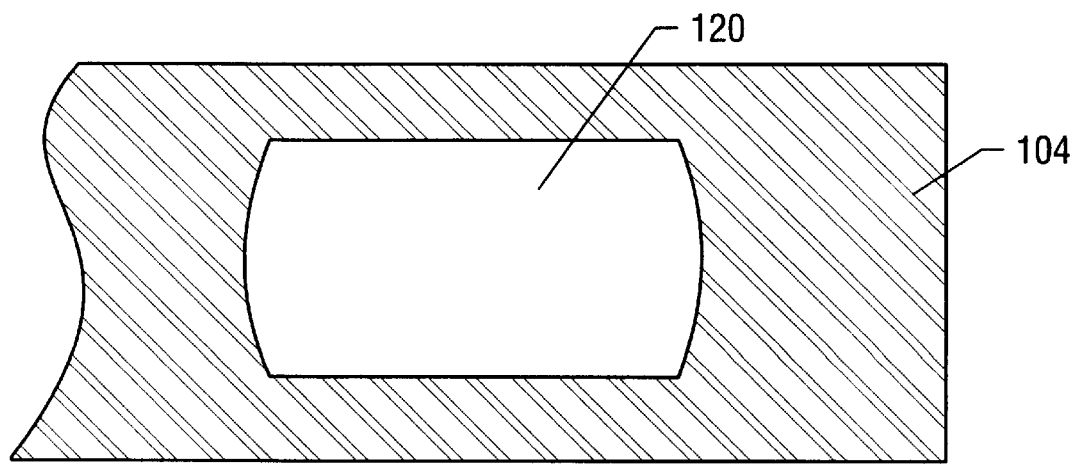
FIG. 1B (prior art) is a top view of a casing for a prior art catheter tip measurement device.

An example of such a prior catheter tip pressure transducer device is shown with reference to FIG. 1A (prior art) and FIG. 1B (prior art), which collectively depict the general structure of a prior device 100. FIG. 1A (prior art) depicts an end cross-section view of a tubular metal casing 104 of a prior catheter tip measurement device 100 in the area that the semiconductor pressure sensor 106 is located. FIG. 1B (prior art) depicts a top view of the metal casing 104 showing a window 120 that exposes the sensing side of the diaphragm on the semiconductor pressure sensor 106 to external pressures.

As mentioned above, a window 120 was generally cut out of tubular metal casing 104. Sensor supports 105 were generally attached to the internal walls of tubular metal casing 104. Once semiconductor pressure sensor 106 was placed inside the tubular metal casing 104 on top of sensor supports 105, a protective material 110 was generally applied to keep body tissues and fluids from contacting the semiconductor pressure sensor 106. Such contact could cause electric shock to the surrounding tissues or damage the pressure sensor. One material that was used as the protective material 110 is flexible room-temperature-vulcanizing (RTV) silicone rubber. This protective material 110 was generally applied over the pressure sensor to a thickness of about 0.002 inches.

Prior catheter tip pressure transducer devices used a metal casing, generally stainless steel, to provide maximum strength to the system with minimal size. Because the system was electrical and the semiconductor pressure sensor was metallic and conductive, the sensor had to be electrically isolated from the metal casing by appropriate internal insulation to avoid electrical contact to bodily tissue through the casing, requiring space inside the tubular metal casing.

In addition, the metal casing generally required further external protection at exposed areas to provide a second barrier to electric shock to the patient and to provide an additional level of sealant against invasion of external fluids. This external sealant was usually in the form of a two part epoxy resin that could be painted on and heat cured as a thin outer coating over the metal casing. Thus, with a semiconductor pressure sensor having an 0.016 inch width, the thickness of the metal casing, the internal insulation and the external sealant led to a minimum outside diameter for a prior catheter tip pressure transducer device of approximately 0.025 inches.

The present invention achieves a drastically reduced feature size that is not possible with prior designs, while still achieving mechanical stability and electrical isolation. The present invention does so by providing a unique and advantageous mounting assembly at the distal tip of a catheter. In particular, rather than the large tubular metal casing, the present invention utilizes a support member for the pressure sensor and a thin layer of insulating material to isolate the support member and the pressure sensor. In this way, mechanical stability and electrical insulation are achieved with drastically reduced size requirements. Thus, the present invention provides reduced size catheter tip strain gauge type pressure transducer devices that may be used in small applications where such devices could not previously be used. More generally, the present invention provides reduced size catheter tip measurement devices.

The present invention may be further understood with reference to the embodiment shown in FIG. 2A, FIG. 2B and FIG. 2C. In particular, FIG. 2A depicts a side cross-section view of a catheter tip measurement device 200 according to the present invention. FIG. 2B depicts an end cross-section view along line A—A of FIG. 2A. Finally, FIG. 2C depicts a top view of a mechanical support member 204 according to the present invention.

Referring to FIG. 2B, a support member 204 provides mechanical stability for the semiconductor pressure sensor 206, and provides a venting channel or access region 216 for allowing reference pressure to reach the pressure sensor 206. Although the support member 204 depicted is generally U-shaped and has a generally planar support surface 224, it is noted that support member 204 may be other shapes and sizes and may have a top width either greater than or less than the width of pressure sensor 206. Preferably, the width of the surface 224 of support member 204 is approximately the size of the width of the pressure sensor 206 to provide good mechanical stability and a small feature size. Pressure sensor 206 may be attached to support surface 224 with a silicon sealant or an epoxy.

Venting channel or access region 216 provides a vent to the back of the semiconductor pressure sensor. Although the shape and size of this vent opening is not significantly important, it must generally be of a sufficient size to equalize the reference side of strain gauge diaphragm of the pressure sensor to the reference pressure. An opening of approximately 0.002 inches or more in diameter is generally required to achieve this venting requirement. An appropriate sized vent opening is generally easy to achieved, for example, by merely leaving a minor space or channel in the support member underneath the pressure sensor 206. Care must be taken, however, that sealant used to cover pressure sensor 206 does not obstruct the venting channel 216. In addition, pressure measurements made within the patient are preferably compared to atmospheric pressure as a reference pressure, rather than compared to a vacuum.

In the embodiment shown, the support member 204 provides a generally planar support surface for the bottom of the semiconductor pressure sensor 206. Support member 204 may be constructed by machining a small-diameter tubular metal casing, such as part of a stainless steel hypodermic needle, to remove approximately the top half of the casing to create a support surface in the area where the measurement device will be placed. FIG. 2C depicts such a structure in that a support surface 224 has been created in area 220 of the tubular metal casing 204 to support semiconductor pressure sensor 206. As also shown in FIG. 2C, the end of the tubular casing may be left in place to provide mechanical strength to the tip of the device. The support member 204 may also be made from non-metal materials, insulating materials and other materials that provide structural stability. For example, a ceramic material with high dielectric insulating properties could be used to provide strong mechanical support for pressure sensor 206 without the need for external insulation over the ceramic support member.

With reference to FIG. 2A, it is shown that the support member 204 may be attached to a catheter 202 by inserting an annular connecting portion 205 into the end of catheter 202. Annular connecting portion 205 may be created by machining the proximal end of a tubular metal casing. The catheter 202 may be attached to connecting portion 205 in a sealed relation by using an epoxy resin, such as Armstrong A-271. If a metal casing is used for support member 204, the connection may be improved by roughing the metal portions that will contact the epoxy, for example by using sand blasting techniques.

Tubular metal casings have been connected to catheter bodies in prior devices. However, in prior devices, the bonding between the metal connecting portions and the catheter is sometimes difficult, as is bonding between the sensor and the casing, even when using a flexible silicone rubber sealant. In particular, flexing of the metal casing within the catheter may cause hair-line cracks to form between the epoxy or flexible sealant and the metal surfaces, allowing fluid to enter the system and potentially degrade system performance. The present invention avoids this problem by using an extremely thin insulating layer 222, which is discussed further below. The insulating layer 222 is preferably made of a polyimide material that is relatively easy to seal to metal and other materials, and thereby provides superior sealant characteristics to protect the measurement sensors from external fluids.

In the embodiment shown, the catheter 202 has an internal lumen 203 that provides venting access to the back of semiconductor pressure sensor 206. This internal lumen 203 allows a reference pressure to contact the reference side of the semiconductor strain gauge diaphragm, which is a part of semiconductor pressure sensor 206. Lumen 203 also provides access for electrical connections 208 to reach semiconductor pressure sensor 206. The catheter may also include additional internal lumens if desired.

In addition, as with prior devices, an epoxy bead 226 may be placed at the distal end of the device, as shown in FIG. 2A, to close the end of the support member 204 and to provide smooth entry characteristics for the catheter tip measurement device. Other measurement devices may be attached to the distal tip of the device. For example, a velocity sensor, such as a Doppler crystal, may attached to the end of support member 204. Electrical connections could run from each side of the Doppler crystal to external processing devices through access region 216 and then through interior lumen 203. A thermistor measurement device could also be attached to the distal tip of support member 204. Such additional measurement devices would provide dual measurement capabilities with pressure sensor 206.

To insulate the semiconductor pressure sensor 206, a flexible insulating material 210 may be applied on top of the pressure sensor 206, as shown in FIG. 2A and FIG. 2B. As with prior devices, this material may be flexible RTV silicone rubber, which is slightly tacky. When used over an opening that needs to be sealed without the material completely filling the internal environment, application of the RTV silicone rubber may be delayed until the material is partially cured. It can then be dabbed into the opening, rather like a putty, and allowed to cure. Once the opening is sealed in this way, further applications may be done with the runnier, completely uncured material. This technique, for example, allows for RTV silicone rubber to be applied to cover pressure sensor 206 without the RTV silicone rubber flowing into an unwanted area, such as venting channel or access region 216.

A flexible insulating material 210 is used to cover the sensing side of the diaphragm of semiconductor pressure sensor 206 to protect and insulate the diaphragm yet still allow the diaphragm to be sensitive to external pressures. RTV silicone rubber, which has good insulating characteristics of approximately 400 volts per mil (mil=1/1000 inches), may be used as this flexible insulating material. It acts as a good sealant and a good insulator without appreciably affecting the pressure signal transmitted to the diaphragm of the pressure sensor.

To insulate the system from body tissues, an insulating layer 222 is applied to surround the measuring tip of the device as shown in FIG. 2A and FIG. 2B. This insulating layer provides a thin outer sheath that isolates and insulates the electrical measurement components with a drastically reduced feature size than that capable in prior designs. If desired, the insulating layer 222 may be applied to cover only the measuring device or other limited electrical portions of the tip of the device. The insulating layer 222 may be achieved using a thin material that has high dielectric insulating characteristics. In particular, the insulating layer 222 may be made using a polyimide sheath or sleeve. Polyimide is a transparent, relatively inert, biocompatible insulating material available in a variety of thicknesses, including wall thicknesses down to 0.0005 inches. Such a polyimide material is available as polyimide tubing from Micro-Lumen in Tampa, Fla. For example, a polyimide sleeve having an 0.017 inch internal diameter and a 0.018 inch outer diameter may be used as insulating layer 222 for a semiconductor pressure sensor having a width of 0.016 inches. The dielectric strength of such a polyimide sleeve may be 4,000 volts per mil, which will effectively insulate the internal parts of the pressure transducer from the outside world.

By using the insulating layer, the insulation limiting factor is now the flexible RTV silicone rubber placed over the pressure sensing diaphragm, rather than the diameter of the metal casing. Generally, the thickness of RTV silicone rubber placed over the pressure sensing diaphragm of the pressure sensor is approximately 2 mils, providing an insulation strength of approximately 600–800 volts. In previous designs, the pressures sensor would first have to be insulated from the internal walls of the metal casing and from body tissues and fluids. By utilizing the thin insulating layer and support member of the present invention, only an extremely thin layer is employed to isolate the electrical and metallic parts of the device, and the volume of the device may be kept very small. The risk of electrical shock is thereby effectively minimized with a drastically reduced feature size.

A window or opening 221 is provided in the insulating layer 222 over the sensing diaphragm region of semiconductor pressure sensor 206. Unlike RTV silicone rubber, polyimide is a rather stiff material and would significantly reduce the pressure transmissions to the pressure sensor if it also covered the sensing diaphragm. Because the RTV silicone rubber bonds very well with polyimide, a particularly good seal is provided at the interface between the polyimide sleeve and the RTV silicone rubber. For example, an oval shaped window may first be made in a polyimide sleeve for opening 221. The polyimide sleeve may next be slipped over the end of the device as insulating layer 221. RTV silicone rubber may then be applied into the window 221 to cover pressure sensor 206 and created an effective seal with the polyimide sleeve.

The advantageous structure of the present invention, therefore, allows outer diameters of 0.018 inches, or better, to be achieved for a catheter tip pressure transducer devices. The outer diameter size possible utilizing the present invention is effectively limited only by the size of the sensing device being supported. As discussed above, prior catheter tip pressure transducer devices have reached an approximate minimum outer diameter of 0.025 inches. This reduction of the diameter from 0.025 inches to 0.018 inches correlates into a reduction in the tip volume size of catheter tip pressure transducer devices by approximately ½ of the previous volume achieved by prior devices.

This drastic reduction in dimensions allows for use of catheter tip pressure transducer devices in a variety of applications that have until now been too small for prior catheter tip pressure transducer devices. Such applications include the use of catheter tip pressure transducer devices in applications where small diameter guidewire is commonly used, such as 0.018 inch guidewire. Another significant small feature size application is in a mouse's heart where the volume of the catheter tip has previously been too large to accurately measure pressure. Utilizing the present invention, the volume of the catheter tip may be made small enough not to appreciably affect the dimensions of the heart of the mice into which the device is placed, thereby allowing accurate measurements to be made where prior devices failed.

Figure 3:
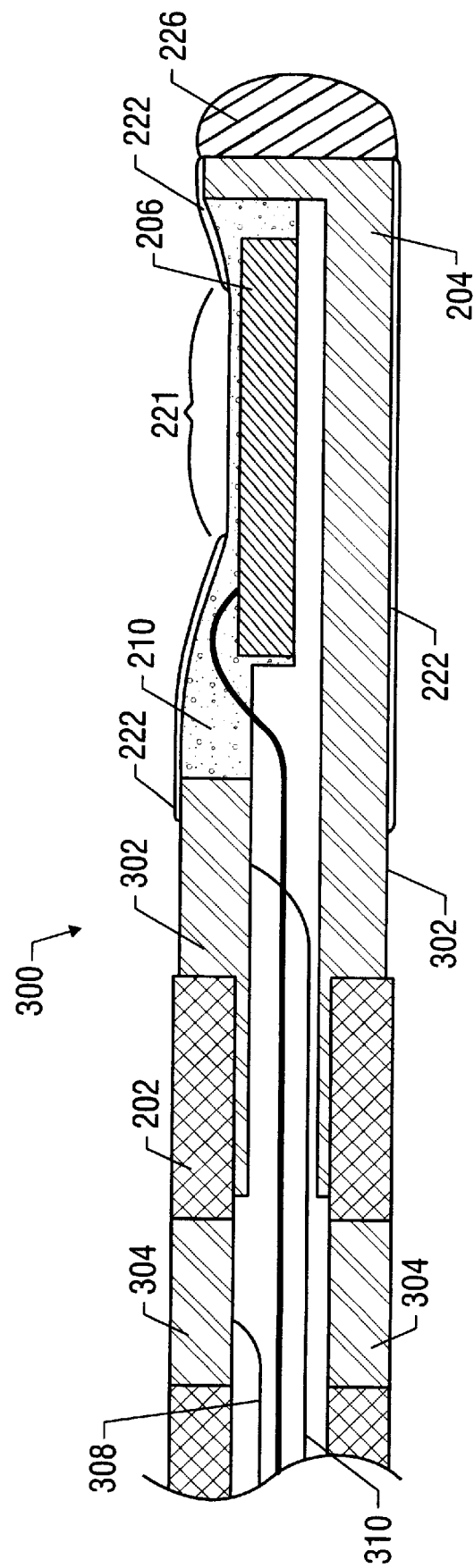
FIG. 3 is a side cross-section view of a catheter tip measurement device with measurement electrodes according to the present invention.

FIG. 3 shows a further embodiment of the present invention in which measurement electrodes are desired to be used in conjunction with pressure measurements. Catheters having external electrodes are commonly used as pacing catheters or as conductance catheters for volumetric measurements. Such catheters have multiple external electrodes that contact internal fluids and tissues. A signal is introduced into the testing environment through the electrodes, and the resulting electrical conduction is measured across the multiple electrodes. Analysis of these measurements are useful and can provide blood volume information as a heart pumps. The present invention may be incorporated into such a multiple electrode catheter.

As shown in FIG. 3, external electrodes, such as external electrode 304, may be provided as part of catheter 202. In addition, if a metal casing is used to create support member 204, part of the polyimide sleeve may be removed from the metal casing to create an additional external electrode 302. For each electrode, additional connection wires are provided, such as electrical connections 308 and 310. Furthermore, an additional electrode (not shown) could be provided at the distal tip of the device beyond the pressure sensor 206. Thus, an electrode catheter may be combined with a pressure sensor utilizing the present invention, and the resulting device will still have an extremely small feature size allowing use in small applications.

One small application for such a device is the measurement of pressure/volume loops in the heart of a very small animal, such as a mouse. Utilizing the structure shown in FIG. 3, the two electrodes 302 and 304 may be used to apply a constant current AC signal across the mouse's heart. A device may then be attached to the electrodes 302 and 304 through electrical connections 308 and 310 to measure the voltage across the electrodes 302 and 304. Such voltage measurements will yield relatively accurate measurements of heart volume simultaneously with high-fidelity pressure measurements provided by the pressure sensor 206. Thus, a single catheter according to the present invention provides simultaneously pressure and volume measurements within the heart of a mouse.

In more general terms, the advantageous structure of the present invention allows for drastic reductions in feature size of existing catheter tip measurement devices that use electrical measurement devices. In particular with reference to FIG. 2B, by using the support surface 224 of the support member 204 as contemplated by the present invention to support an electrical measurement device, and by using a thin insulating layer 221 to electrically isolate and insulate the electrical measurement sensor 206 from surrounding tissues, the feature size of catheter tip measurement devices may be significantly reduced. The outer diameters of such device utilizing the present invention may be made approximately the same size as the width of the measurement sensor. Thus, the present invention may be advantageously applied to catheter tip measurement devices to alleviate the need for placing the measurement sensor inside of a protective tubular metal casing. Thus, the present invention has advantageous applications to catheter tip measurement devices in general.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having the benefit of this description of the invention.

What is claimed is:

1. A catheter tip pressure transducer device, comprising:
   a catheter body having at least one internal lumen providing access to an external reference pressure;
   at least one electrode disposed adjacent a distal end of said catheter body;
   a support member coupled to a distal tip of said catheter body, said support member having a support surface, wherein said support member comprises metal, and wherein a portion of said support member comprises said at least one electrode;
   a venting channel disposed within said support surface of said support member in communication with said at least one internal lumen of said catheter body;
   a semiconductor pressure sensor having a diaphragm with a sensing side and a reference side, said pressure sensor being supported by said support surface of said support member and positioned relative to said venting channel so that said reference side of said diaphragm is in communication with said venting channel;
   a flexible insulating material disposed over said sensing side of said diaphragm of said pressure sensor; and
   an outer insulating layer covering exposed areas of said pressure sensor except for said diaphragm of said pressure sensor.

2. The catheter tip pressure transducer device of claim 1 further comprising at least one additional electrode disposed in said catheter body.

3. The catheter tip pressure transducer device of claim 1, wherein said outer insulating layer surrounds the distal tip of said device including said support member and said pressure sensor.

4. The catheter tip pressure transducer device of claim 3, wherein said outer insulating layer comprises a polyimide sleeve.

5. The catheter tip pressure transducer device of claim 1, wherein said support surface of said support member is a generally planar support surface.

6. The catheter tip pressure transducer device of claim 1, wherein said support surface of said support member comprises the top of a generally U-shaped member.

7. The catheter tip pressure transducer device of claim 1, wherein said support member comprises a tubular metal casing including a generally U-shaped portion providing said support surface with said venting channel.

8. The catheter tip pressure transducer device of claim 7, wherein said generally U-shaped portion is disposed adjacent a distal end of said tubular metal casing.

9. The catheter tip pressure transducer device of claim 1, wherein said outer insulating layer is a polyimide material.

10. The catheter tip pressure transducer device of claim 1, wherein the width of said support surface of said support member is approximately the width of said semiconductor pressure sensor.

11. The catheter tip pressure transducer device of claim 1, wherein a distal tip of said device has an outer diameter of approximately the width of said semiconductor pressure sensor.

12. The catheter tip pressure transducer device of claim 1, wherein a distal tip of said device has an outer diameter of approximately 0.018 inches or less.

13. The catheter tip pressure transducer device of claim 1, further comprising an epoxy bead coupled to a tip of said support member.

* * * * *